United States Patent [19]
Wilson et al.

[11] Patent Number: 6,057,306
[45] Date of Patent: May 2, 2000

[54] METHOD OF TREATING THE NAVICULAR DISEASE IN HORSES

[75] Inventors: Alan Martin Wilson, Bayford; Allen Edward Goodship, Hertfordshire, both of United Kingdom; Jonathan Green, Arlesheim, Switzerland

[73] Assignee: Novartis Corporation, New York, N.Y.

[21] Appl. No.: 09/043,842

[22] PCT Filed: Sep. 24, 1996

[86] PCT No.: PCT/EP96/04161

§ 371 Date: May 15, 1998

§ 102(e) Date: May 15, 1998

[87] PCT Pub. No.: WO97/12619

PCT Pub. Date: Apr. 10, 1997

[30] Foreign Application Priority Data

Sep. 29, 1995 [CH] Switzerland ............................ 2760/95

[51] Int. Cl.[7] ................................................. A61K 31/66
[52] U.S. Cl. ........................ 514/102; 514/108; 514/112; 424/442
[58] Field of Search ..................... 424/422, 438, 424/442; 514/102, 108, 112, 114, 126, 129, 131

[56] References Cited

U.S. PATENT DOCUMENTS

| | | | |
|---|---|---|---|
| 3,962,432 | 6/1976 | Schmidt-Dünker ...................... | 424/204 |
| 4,086,334 | 4/1978 | Schmidt-Dünker et al. ........... | 424/177 |
| 4,687,767 | 8/1987 | Bosies et al. ............................... | 514/89 |
| 4,746,654 | 5/1988 | Breliere et al. .......................... | 514/108 |
| 4,784,993 | 11/1988 | Boises et al. ............................... | 514/93 |
| 4,876,248 | 10/1989 | Breliere et al. .......................... | 514/108 |
| 4,927,814 | 5/1990 | Gall et al. ................................ | 514/108 |
| 4,939,130 | 7/1990 | Jaeggi et al. ............................... | 514/94 |
| 5,057,505 | 10/1991 | Widler et al. .............................. | 514/80 |
| 5,376,647 | 12/1994 | Sohda et al. ............................... | 514/89 |
| 5,512,552 | 4/1996 | Sohda et al. ............................. | 514/102 |

FOREIGN PATENT DOCUMENTS

| | | |
|---|---|---|
| 0 243 173 | 10/1987 | European Pat. Off. . |
| 21 30 794 | 1/1973 | Germany . |

OTHER PUBLICATIONS

Colles C. (1982) "Navicular disease and its treatment" In Practice, 3:29–36.
Devous MD, et al. (1984) "Techniques and applications of nuclear medicine in the diagnosis of equine lameness" JAVNA 184(3):318–325.
Fleisch H. (1991) "Bisphosphonates, Pharmacology and Use in the Treatment of Tumour–Induced Hypercalcaemic and Metastic Bone Disease" Drugs, v42(6):919–944.
Hümpel P, et al. (1991) ZK 90 695: "A new antiarthritic drug and tissue targeting properties" Agents and Actions v32 (1/2):22–23.
Leach, D–H. (1993) "Treatment and pathogenesis of navicular disease ('syndrome')" Equine Vet J, 25(6):477–481.
Lepage OM, et al. (1988) "L'emploi d'un bisphosphonate (ADP) dans la prévention des exostoses chex le poney Shetland. Etude prélimimaire" Ann M´´d Vét, 132:391–399.
MacGregor CM (1989) Editorials, "Navicular disease—in search of definition" Equine Vet J, v21(6):389–391.
Ostblom L, et al. (1989) "Navicular bone disease: a comparative histomorphometric study" Equine Vewt J, V21(6):431–433.
Ostblom L, et al. (1982) "Histological study of navicular bone disease" Equine Vet J, v14(3):199–202.
Patel S, et al. (1993) "Drugs Used in the Treatment of Metabolic Bone Disease: Clinical Pharmacology and Therapeutic Use" Drugs, 46(4):594–617.
Pollitt C. (1990) "Navicular Disease" Veter, Continuing Education. 5:99–114.
Trotter GW. (1991) "Therapy for Navicular Disease" The Compendium on Continuing Education for Practicing Veter, v13(9):1462–1466.
Turner TA. (1986) "Shoeing principles for the management of navicular disease in horses" JAVMA, v189(3):298–301.
Turner TA. (1989) "Diagnosis and Treatment of the Navicular Syndrome in Horses" Veterinary Clinics of North America: Equine Practice, v5(1): 131–144.
Van Beek E, et al. (1994) "Structural Requirements for Bishosphonate Actions In Vitro" J of Bone and Mineral Research, v9(12): 1875–1882.
Van Gelder JM, et al. (1995) "Anticalcification and Antiresorption Effects of Bisacyphosphonates" Bone, v16(5):511–520.
Wright IM, et al. (1993) "Biomechanical considerations in the treatment of navicular disease" The Veterinary Record, 133:109–114.

*Primary Examiner*—Neil S. Levy
*Attorney, Agent, or Firm*—Michael P. Morris

[57] ABSTRACT

The invention relates to a method of treating the navicular disease in horses, which comprises treating the navicular disease in horses with an effective amount of at least one compound of formula (I),

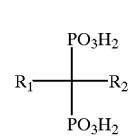

(I)

wherein $R_1$ is hydrogen, hydroxy, amino or halogen, and $R_2$ is hydrogen, halogen or a radical which is bound through C, N, S or O, or of a $C_1$–$C_4$ tetraalkyl ester thereof, each in the free form or in the form of the salt and/or in the hydrate form; to a compound of formula (I) for use in a method of treating the navicular disease, to a composition for use in a method of treating the navicular disease, which comprises one or more than one compound of formula (I), as well as to the use of a compound of formula (I) for the preparation of a veterinary composition for treating the navicular disease.

8 Claims, No Drawings

METHOD OF TREATING THE NAVICULAR DISEASE IN HORSES

The present invention relates to a method of treating the navicular disease in horses, which comprises treating the navicular disease in horses with an effective amount of at least one compound of formula

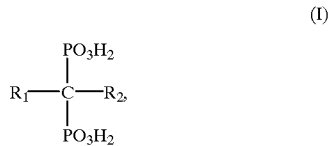

(I)

wherein $R_1$ is hydrogen, hydroxy, amino or halogen, and $R_2$ is hydrogen, halogen or a radical which is bound through C, N, S or O, or of a $C_1$–$C_4$-tetraalkyl ester thereof, each in the free form, in the form of the salt and/or in the hydrate form; to a compound of formula I for use in a method of treating the navicular disease, to a composition for use in a method of treating the navicular disease, which comprises one or more than one compound of formula I, as well as to the use of a compound of formula I for the preparation of a veterinary composition for treating the navicular disease.

The navicular disease is a common cause of lameness in horses. The disease has to be treated by elaborate methods but nevertheless almost always results in the loss of the affected, but otherwise healthy, horse. The disease strikes all horse races and usually occurs in 6–12-year-old horses. The disease starts insidiously but can be detected without exception already at a stage in which the horse does not show any symptoms yet.

The pathophysiology of the navicular disease is not at all clear. Among the numerous theories regarding its etiology, two are of preeminent interest: Bad blood circulation in the foot is blamed on the one hand and changes in the biomechanical properties of the foot, i.e. the navicular bone, of the horses are blamed on the other hand. Correspondingly, there are primarily two methods of treatment which are often employed: The biomechanical explanation of the disease calls for corresponding measures of the farrier as well as for chirurgical methods. The blood circulation theory, on the other hand, rather indicates drug treatment of the horse which aims at improving the blood circulation in the navicular bone but also in the surrounding tissue. Attempts have therefore been made to achieve an improvement using anticoagulants. e.g. warfarin. The inflammation of the affected bone is also treated with steroidal and nonsteroidal antiinflammatory drugs. However, these methods are only partly successful, their efficiency is difficult to assess, they are elaborate and, in particular, they do not achieve a permanent cure of the disease. Accordingly, there is still an urgent need to solve the problem.

Surprisingly, it has now been found that the disease can be treated efficiently and with lasting effect with bisphosphonates of the above formula (I). It is known that bisphosphonates of the type of this invention have no, or only very little, influence on the blood flow and have only extremely limited antiinflammatory properties. It therefore has to be considered as particularly surprising that of all compounds these are capable of solving the problem so substantially. It has also been found that the bisphosphonates of the above formula (I) have a pronounced effect on the bone cyst like lesions that occur under the pathophysiology of navicular bone disease. They very effectively remodel the wounded bone. A particularly important advantage of the compounds of formula I is their relatively long duration of efficacy. Because the navicular disease in horses is a problem which has been known for a long time and which can cause the animal owner great losses, intense searches for solutions have already been conducted and the novel treatment of the disease with bisphosphonates of formula I is therefore particularly remarkable.

Within the scope of this invention a preferred method of treating the navicular disease in horses is that which comprises using one or more than one compound of formula (I), wherein either $R_1$ and $R_2$ are each independently of the other halogen, or $R_1$ is hydrogen, $R_2$ is a Ar—S—, Het—NH—, $C_3$–$C_7$cycloalkyl-NH—, Ar—S—A—N($R_3$)—, Het—S—A—N($R_3$)— or —C(=S)NH$C_6H_5$ group, A is linear or branched $C_1$–$C_{12}$alkyl, Ar is unsubstituted or substituted phenyl, Het is unsubstituted or substituted monocyclic 5- or 6-membered monoaza-, diaza- or thiazaaryl, which is bound through a ring-carbon atom or a ring-nitrogen atom, $R_3$ is hydrogen or $C_1$–$C_{12}$alkyl; or $R_1$ is hydrogen or hydroxy, $R_2$ is $R_4$—A—, $R_4$ is Ar, Het or —N($R_5$)($R_6$), A is linear or branched $C_1$–$C_{12}$alkyl, Ar is unsubstituted or substituted phenyl, and Het is unsubstituted or substituted monocyclic 5- or 6-membered monoaza-, diaza- or thiazaaryl, which is bound through a ring-carbon atom or a ring-nitrogen atom, $R_5$ and $R_6$ are each independently of the other hydrogen, $C_1$–$C_6$alkyl, $C_3$–$C_7$cycloalkyl, Ar—$C_1$–$C_6$alkyl, Ar—O—$C_1$–$C_6$alkyl, Ar—S—$C_1$–$C_6$alkyl or Het—$C_1$–$C_6$alkyl, or two alkyl $R_5$ and $R_6$ together form a 4 to 7-membered bridge which is unsubstituted or substituted by Ar and wherein two carbon atoms can by linked by a further $C_1$–$C_6$alkyl bridge, as well as using the two compounds 5-benzoyl-3,4-dihydro-2H-pyrazole-3,3-diphosphonic acid tetraethyl ester and (N-{4-phenylthion-butyl})aminomethanediphosphonic acid tetraethyl ester, in the free form or in the form of the salt, a hydrate thereof or a salt of a hydrate, which process comprises treating said disease in horses with an effective amount of such a compound.

Within the scope of this invention, the pharmaceutically acceptable alkanebisphosphonic acid derivatives of formula I can be present in the form of isomers, typically as optical isomers, e.g. a pure diastereomers or diastereomer mixtures.

Salts of compounds of formula I are in particular pharmaceutically acceptable salts, e.g. acid addition salts which are typically formed with strong inorganic acids such as mineral acids, e.g. sulfuric acid, a phosphoric acid or a hydrohalic acid, with strong organic carboxylic acids, typically lower alkanecarboxylic acids, e.g acetic acid, such as saturated or unsaturated dicarboxylic acids, typically malonic acid, maleic acid or fumaric acid, or hydroxycarboxylic acids, typically tartaric acid or citric acid, or with sulfonic acids, e.g. lower alkane sulfonic acids or unsubstituted or substituted benzenesulfonic acids, typically methanesulfonic acid or p-toluenesulfonic acid, or salts with bases, such as corresponding alkali metal salts or alkaline earth metal salts, e.g. sodium salts, potassium salts or magnesium salts, pharmaceutically acceptable transition metal salts, for example zinc or copper salts, or salts with ammonia or organic amines, e.g. cyclic amines, typically mono-, di- or trilower alkylamines, such as hydroxy-lower alkylamines, typically mono-, di- or trihydroxy-lower alkylamines, hydroxy-lower alkyl-lower alkylamines or polyhydroxy-lower alkylamines. Cyclic amines are typically morpholine, thiomorpholine, piperidine or pyrrolidine. Mono-lower alkylamines may suitably be ethylamine and t-butylamine, and di-lower alkylamines may suitably be diethylamine and diisopropylamine, and tri-lower alkylamines may suitably be trimethylamine and trethylamine. Corresponding hydroxy-lower alkylamines are typically mono-, di- and triethanolamine; hydroxy-lower alkyl-lower alkylamines are e.g. N,N-dimethylaminoethanol and N,N-diethylaminoethanol; polyhydroxy-lower alkylamine is suitably e.g. glucosamine. Accordingly, the term "compounds of formula I" will be taken to mean hereinabove and hereinbelow the free compounds of formula I as well as their salts and also the hydrates of the free compounds of formula I and their salts. Preferred are, on the one hand, the free acids and, on the other hand, the disodium salts of the compounds of formula I.

Alkyl, as group per se and also as structural element of other groups such as of Ar-alkyl, Ar—O-alkyl, Ar—S-alkyl, Het-alkyl or alkoxy, is either straight-chain, typically methyl, ethyl, n-propyl, n-butyl, n-hexyl, n-octyl, n-decyl or n-dodecyl, or branched, typically isopropyl, isobutyl, sec-butyl, tert-butyl, isopentyl, neopentyl or isohexyl, depending in each case on the number of carbon atoms in the corresponding group. $C_1$14 $C_4$Alkyl is preferred, in particular linear $C_1$–$C_4$alkyl, very particularly methyl and ethyl.

Cycloalkyl is cyclopropyl, cyclobutyl, cyclopentyl, cyclohexyl or cycloheptyl.

Phenyl is either unsubstituted or mono- or polysubstituted and is typically independently of one another substituted by one, two or three $C_1$–$C_4$alkyl, $C_1$–$C_4$alkoxy, trifluoromethyl and halogen, and monosubstituted phenyl as well as unsubstituted phenyl is particularly preferred, in particular phenyl which is monosubstituted by halogen, preferably by chloro.

Monocyclic 5- or 6-membered monoaza-, diaza- or thiazaaryl is typically pyrrolyl; imidazolyl, such as 1-, 2- or 4-imidazolyl; pyrazolyl, such as 1- or 3-pyrazolyl; thiazolyl, such as 2- or 4-thiazolyl; pyridyl, such as 2-, 3- or 4-pyridyl. The corresponding heterocyclic radicals can be substituted by one or more than one, typically 1–3, preferably 1, $C_1$–$C_4$alkyl group. Preferred substituted heterocyclic radicals of this type are, for example, $C_1$–$C_4$alkyl-substituted 1-imidazolyl and 4-imidazolyl, 5–$C_1$–$C_4$alkyl-2-thiazolyl, such as 5-methyl-2-thiazolyl, 5-ethyl-2-thiazolyl and 5-n-butyl-2-thiazolyl, and also $C_1$–$C_4$alkyl-substituted 2- and 3-pyridyl.

Unsubstituted or substituted bicyclic monoaza-, diaza- or triazaaryl is typically imidazo[1,2-a]pyridyl, such as imidazo[1,2-a]pyridin-3-yl.

Preferred $R_5$ and $R_6$ are hydrogen, $C_1$–$C_4$alkyl, $C_3$–$C_6$cycloalkyl, phenyl-$C_1$–$C_4$alkyl, $C_1$–$C_4$-alkylphenyl-$C_1$–$C_4$alkyl diphenyl-$C_1$–$C_4$alkyl, phenoxy-$C_1$–$C_4$alkyl, alkylphenoxy-$C_1$–$C_4$alkyl, diphenoxy-$C_1$–$C_4$alkyl, phenylthio-$C_1$–$C_4$alkyl, $C_1$–$C_4$alkylphenylthio-$C_1$–$C_4$alkyl, diphenylthio-$C_1$–$C_4$alkyl, pyridyl-$C_1$–$C_4$alkyl, $C_1$–$C_4$alkylpyridyl-$C_1$–$C_4$alkyl, or dipyridyl-$C_1$–$C_4$alkyl, where the phenyl and pyridyl radicals can be substituted as indicated above.

Alkyl $R_5$ and $R_6$, which together form a 4- to 7-membered bridge are, together with the linking nitrogen atom, preferably pyrrolidin-1-yl, piperidin-1-yl, 2-(4-chlorophenyl) piperidin-1-yl, 3-phenylpiperidin-1-yl or 3-phenylpyrrolidin-1-yl.

In the case of two alkyl $R_5$ and $R_6$, which together form a 4- to 7-membered bridge, wherein two carbons atoms are linked by one further $C_1$–$C_6$alkyl bridge, 2 non-adjacent carbon atoms are preferably linked with each other, in particular through methylenes. Corresponding 3-azabicyclo-$C_6$–$C_{10}$alk-3-yl radicals are preferred.

Halogen is fluoro, chloro, bromo or iodo, preferably fluoro, chloro or bromo, in particular chloro.

The pharmaceutically valuable alkanebisphosphonic acid derivatives of the above formula I are known and can be prepared by known processes, such as those mentioned, inter alia, in EP-A-100718, EP-A-274346, EP-A-275821, EP-A-170228, EP-A-252505, DE-OS-2405254, EP-A-243173, and EP-A-464509.

A preferred embodiment of this invention is a method of treating the navicular disease with a compound of formula I, wherein $R_1$ and $R_2$ are each independently of the other chloro, bromo or iodo, preferably chloro, in the free form or in the form of the salt, a hydrate thereof, a salt of a hydrate or a $C_1$–$C_4$alkyl ester thereof.

Another preferred embodiment of this invention is a method of treating the navicular disease in horses with a compound of formula I, wherein $R_1$ is hydrogen, and $R_2$ is Ar—S—, Het—NH—, cyclo-$C_3$–$C_7$—NH—, Ar—S—A—NH—, Het—S—A—NH— or $C_6H_5$—NHC(=S)—, A is linear or branched $C_1$–$C_6$alkyl, Ar is unsubstituted phenyl or phenyl which is independently of one another substituted by one or two $C_1$–$C_4$alkyl, $C_1$–$C_4$alkoxy, trifluoromethyl or halogen, Het is unsubstituted thiazolyl or pyridyl, or thiazolyl or pyridyl which is substituted by $C_1$–$C_4$alkyl and wherein, very particularly, $R_1$ is hydrogen, and $R_2$ is $C_6H_5$—NHC(=S)—, unsubstituted or chloro-substituted phenylthio, unsubstituted or $C_1$–$C_4$alkyl-substituted thiazolylamino or cycloheptylamino.

Another preferred embodiment of this invention is a method of treating the navicular disease in horses with a compound of formula I, wherein $R_1$ is hydrogen or hydroxy, $R_2$ is $R_4$—A—, $R_4$—N($R_5$)($R_6$), and $R_5$ and $R_6$ are each independently of the other hydrogen, $C_1$–$C_4$alkyl, cyclo-$C_3$–$C_7$alkyl, Ar—$C_1$–$C_4$alkyl, Ar—O—$C_1$–$C_4$alkyl, Ar—S—$C_1$–$C_4$alkyl or pyridyl-$C_1$–$C_4$alkyl, or wherein two alkyl $R_5$ and $R_6$ together form a 4- to 7-membered bridge which is unsubstituted or substituted by Ar and wherein two carbon atoms can be linked to each other by a further $C_1$–$C_6$alkyl bridge and wherein, very particularly preferably, $R_1$ is hydrogen or hydroxy, $R_2$ is $R_4$—A—, A is $C_1$–$C_5$alkyl, and $R_4$ is $NH_2$, dimethylamino, N-methyl-N-n-propylamino, N-methyl-N-n-pentylamino, N-cycloheptylamino, N-methyl-N-(2-phenylethyl)amino, N-methyl-N-(3-phenylpropyl)amino or N-methyl-N-(5-phenylpentyl) amino, N-methyl-N-(3-phenoxypropyl)amino, N-methyl-N-(2-phenylthioethyl)amino, N-methyl-N-(3-phenylthiopropyl)amino, N-methyl-N-[3-(2-pyridyl) propyl]amino, piperidin-1-yl, which is unsubstituted or substituted in 4-position by phenyl, or pyrrolidin-1-yl which is unsubstituted or substituted in 3-position by 4-chlorophenyl, or 1,5-dimethyl-3-azabicyclo[3.1.1 ]hept-3-yl, in the free form or in the form of the salt, a hydrate thereof or a salt of a hydrate.

The invention relates in particular to a method of treating the navicular disease in horses with (1) 3-amino-1-hydroxypropane-1,1-diphosphonic acid (pamidronic acid); or
(2) 3-(N,N-dimethylamino)-1-hydroxypropane-1,1-diphosphonic acid; or
(3) 4-amino-1-hydroxybutane-1,1-diphosphonic acid (alendronic acid); or
(4) 6-amino-1-hydroxyhexane-1,1-diphosphonic acid, e.g. amino-hexyl-BP; or
(5) 3-(N-methyl-N-n-pentylamino)-1-hydroxypropane-1,1-diphosphonic acid; or
(6) 1-hydroxy-2-(imidazol-1-yl)ethane-1,1-diphosphonic acid; or
(7) 1-hydroxy-2-(pyrid-3-yl)ethane-1,1-diphosphonic acid (risedronic acid); or
(8) 4-chlorophenylthiomethanediphosphonic acid (tiludronic acid); or
(9) 3-(N-2-phenylthioethyl-N-methylamino)-1-hydroxypropane-1,1-diphosphonic acid; or
(10) 1-hydroxy-3-(pyrrolidin-1-yl)propane-1,1-diphosphonic acid; or
(11) 3-(3-[4-chlorophenyl]pyrrolidin-1-yl)1-hydroxypropane-1,1-diphosphonic acid; or
(12) (N-cycloheptylamino)methanediphosphonic acid; or
(13) (N-phenylaminothiocarbonyl)methanediphosphonic acid; or
(14) 5-benzoyl-3,4-dihydro-2H-pyrazole-3,3-diphosphonic acid tetraethyl ester; or
(15) 1-hydroxy-2-(imidazo[1,2-a]pyridin-3-yl)ethane-1,1-diphosphonic acid; or
(16) dichloromethanediphosphonic acid (clodronic acid); or
(17) 3-(N-methyl-N-3-phenyl-n-propylamino)-1-hydroxypropane-1,1-diphosphonic acid; or
(18) 3-(N-methyl-N-5-phenyl-n-pentylamino)-1-hydroxypropane-1,1-diphosphonic acid; or
(19) 3-(N-methyl-N-[5-pyrid-2-yl]-n-pentylamino)-1-hydroxypropane-1,1-diphosphonic acid; or
(20) 3-(N-methyl-N-[3-phenoxy]-n-propyl-amino)-1-hydroxypropane-1,1-diphosphonic acid; or
(21) 3-(N-methyl-N-[2-phenoxy]ethylamino)-1-hydroxypropane-1,1-diphosphonic acid; or
(22) 4-(4-phenyl)piperidin-1-yl-1-hydroxybutane-1,1-diphosphonic acid; or
(23) 1-hydroxy-3-piperidin-1-yl-propane-1,1-diphosphonic acid; or
(24) 3-(4-[4-chlorophenyl]piperidin-1-yl)-1-hydroxypropane-1,1-diphosphonic acid; or
(25) (5-n-butyl)thiazol-2-yl-methanediphosphonic acid; or
(26) (5-methyl)thiazol-2-yl-methanediphosphonic acid; or
(27) thiazol-2-yl-methanediphosphonic acid; or
(28) (5-ethyl)thiazol-2-yl-methanediphosphonic acid; or
(29) 1-hydroxy-(N-[2-phenyl]ethyl-N-methylamino)propane-1,1-di phosphonic acid; or
(30) 3-(N-methyl-N-[3-phenylthio]-n-propylamino)-1-hydroxypropane-1,1-diphosphonic acid; or
(31) 2-(N,N-dimethylamino)-1-hydroxyethane-1,1-diphosphonic acid; or
(32) 3-(N-methyl-N-n-propylamino)-1-hydroxypropane-1,1-diphosphonic acid; or
(33) 1-hydroxy-3-(N-[3-phenylthio]n-propyl-N-methyl-amino)propane-1,1-diphosphonic acid; or
(34) 1-hydroxy-3-(N-[4-phenylthio]n-butyl-N-methylamino)propane-1,1-diphosphonic acid; or
(35) 2-(1-methyl)imidazol-2-yl-ethane-1,1-diphosphonic acid; or
(36) 1-hydroxy-2-(4-methyl)imidazol-5-yl-ethane-1,1-diphosphonic acid; or
(37) 1-hydroxy-2-(imidazol-5-yl)ethane-1,1-diphosphonic acid; or
(38) 2-(pyrid-2-yl)ethane-1,1-diphosphonic acid; or
(39) 3-(1,5-dimethyl-3-azabicyclo[3.1.1]hept-3-yl)-1-hydroxypropane-1,1-diphosphonic acid; or
(40) (4-phenylthio-n-butylamino)methanediphosphonic acid tetraethyl ester, in the free from or in the form of the salt, a hydrate thereof, a pharmaceutically acceptable salt or a salt of a hydrate.

A very particularly preferred method of controlling the navicular disease in horses is, on the one hand, that using 3-amino-1-hydroxypropane-1,1-diphosphonic acid, in the free form or in the form of the salt as well as the hydrates of the free acid or the salts thereof, very particularly with 3-amino-1-hydroxypropane-1,1-diphosphonic acid disodium salt pentahydrate (disodium pamidronate pentahydrate) and, on the other hand, that using 1-hydroxy-2-(imidazol-1-yl)ethane-1,1-diphosphonic acid, in the free form or in the form of the salt as well as the hydrates of the free acid or the salts thereof, very particularly with 1-hydroxy-2-(imidazol-1-yl)ethane-1,1-diphosphonic acid monohydrate.

The alkanebisphosphonic acid derivatives are preferably used in the form of compositions containing a pharmaceutically effective amount of the active ingredient, typically together with suitable inorganic or organic, solid or liquid carriers.

The pharmaceutical compositions can be used, for example, for enteral, e.g. oral, rectal or nasal administration, for parenteral, e.g. intravenous or subcutaneous administration, or for transdermal (for example passive or iontophoretic) administration. Direct local administration to the foot of the animal is also suitable. The intravenous treatment is preferred.

Accordingly, the invention also relates to a composition comprising as active ingredient one or more than one compound of formula I or a salt thereof which is tolerated by horses and at least one carrier, in an amount effective for treating the navicular disease. These pharmaceutical compositions are used for enteral, e.g. oral, and also rectal, administration, as well as for parenteral and for local administration and contain the pharmacological compounds singly or together with conventional pharmaceutical excipients. The pharmaceutical compositions contain typically from about 0.001% to 100% by weight, preferably from about 0.1% to about 50% by weight, of the compound.

Pharmaceutical compositions for enteral and parenteral administration are, for example, those in dosage unit forms, such as dragées, tablets, capsules or suppositories and also ampoules. They are prepared in a manner known per se, typically using conventional mixing, granulating, confectioning, solubilising or lyophilising methods. Accordingly, pharmaceutical compositions for oral administration can be obtained by combining the active ingredient with solid carriers, where appropriate granulating a resulting mixture, and by processing the mixture or granulate, if desired or necessary after the addition of suitable excipients, into tablets or dragée cores.

Suitable carriers are in particular fillers, typically sugar, e.g. lactose, saccharose, mannitol or sorbitol, cellulose preparations and/or calcium phosphates, such as tricalcium phosphate or calcium hydrogen phosphate, as well as binders, e.g. starch pastes, using, for example, corn, wheat, rice or potato starch, gelatin, tragacanth, methylcellulose and/or polyvinylpyrrolidone and, where desired, disintegrators, such as the above-mentioned starches, and also carboxymethyl starch, crosslinked polyvinylpyrrolidone, agar or alginic acid or a salt thereof, such as sodium alginate. Excipients are primarily flow control agents and lubricants, typically silicic acid, talcum, stearic acid or salts thereof, such as magnesium stearate or calcium stearate, and/or polyethylene glycol. Dragée cores are provided with suitable coatings, which may be resistant to gastric juices, using, inter alia, concentrated sugar solutions which optionally contain gum arabic, talcum, polyvinylpyrrolidone, polyethylene glycol and/or titanium dioxide, or coating solutions in suitable organic solvents or solvent mixtures or, for the preparation of gastric juice-resistant coatings, solutions of suitable cellulose preparations, such as acetylcellulose phthatate or hydroxypropylmethylcellulose phthalate. Colourants or pigments can be added to the tablet or dragée coatings e.g. for the purpose of identification or to indicate different doses of active ingredient.

Other pharmaceutical compositions for oral administration are dry-filled capsules made of gelatin as well as soft, sealed capsules made of gelatin and a plasticiser, such as a glycerol or sorbitol. The dry-filled capsules may contain the active ingredient in the form of a granulate, typically in admixture with fillers, such as lactose, binders, such as starches, and/or lubricants, such as talcum or magnesium stearate, and where appropriate, stabilisors. In soft capsules, the active ingredient is preferably dissolved or suspended in suitable liquids, such as fatty oils, paraffin oil or liquid polyethylene glycols, with the possible addition of stabilisors.

Suitable compositions for rectal administration are typically suppositories consisting of a combination of the active ingredient with a suppository base material. Suitable suppository base materials are, for example, natural or synthetic triglycerides, paraffin hydrocarbons, polyethylene glycols or higher alkanoles. Gelatin rectal capsules can also be used which contain a combination of the active ingredient with a base material. Base materials can be e.g. liquid triglycerides, polyethylene glycols or paraffin hydrocarbons.

Suitable for parenteral administration are primarily aqueous solutions of an active ingredient in water-soluble form, e.g. a water-soluble salt, as well as suspensions of the active ingredient, such as corresponding oily injection suspensions, using suitable lipophilic solvents or vehicles, such as fatty oils, e.g. sesame oil, or synthetic fatty acid esters, typically ethyl oleate or triglycerides, or aqueous injection suspensions which contain viscosity-increasing substances, typically sodium carboxymethylcellulose, sorbitol and/or dextran, and optionally also stabilisors.

Pharmaceutical compositions for local administration are, for example for the topical treatment of the skin, lotions, creams and ointments, i.e. liquid or semisolid oil-in-water or water-in-oil emulsions, fatty anhydrous ointments; pastes, i.e. creams and ointments containing secretion-absorbing powder components; gels which are watery, low in water or water-free and consisting of swellable gel-forming materials; foams, i.e. liquid oil-in-water emulsions in aerosol form which are administered from pressure vessels, and tinctures having an aqueous-ethanolic base, each of which can contain additional customary pharmaceutical excipients, such as preservatives. The preparation of the pharmaceutical compositions for oral administration is carried out in a manner known per se by mixing the active ingredient with the pharmaceutical excipients, typically by dissolving or suspending the active ingredient in the base or in part of the base, if required. For the preparation of the emulsions, wherein the active ingredient is dissolved in one of the liquid phases, the active ingredient is usually dissolved in the phase before emulsification; for the preparation of suspensions, in which the active ingredient is suspended in the emulsion, the active ingredient is mixed with part of the base after emulsification and then added to the remaining formulation.

The dose of the active ingredient can depend on different factors, such as efficiency and duration of efficacy, the severity of the disease and its symptoms, mode of application, race, gender, age, weight and/or individual state of the horse. The compounds of formula I are preferably administered in amounts customary for treating other bone diseases, also in man. In normal treatment the horse is given 0.1 mg to 200 mg, preferably 0.1 mg to 100 mg, more preferably 0.2 mg to 10 mg, very particularly preferably 0.5 mg to 5 mg, most preferably 0.5 mg, of the active ingredient per kg of body weight, where required in several, optionally identical, divided doses. Said doses are administered to the horse daily or, for example, one, three or four times, preferably once a week, preferably intravenously. It is very particularly preferred to treat the horse with a total of 2 mg of the active ingredient in four doses at 0.5 mg each, which are administered over a period of 4 weeks at intervals of one week.

EXAMPLES A To F

Pharmaceutical Compositions

Hereinbelow, the term "active ingredient" will be understood to mean a compound of formula I, in the free form or in the form of a pharmaceutically acceptable salt or a hydrate of such a compound in the free form or in the form of a salt, in particular a compound (1) to (39).

Example A: Ampoule comprising disodium pamidronate pentahydrate dissolved in water. After dilution (concentration 3 mg/ml), the solution is suitable for an intravenous infusion.

Composition:

| | |
|---|---|
| active ingredient | 19.73 mg (15.0 mg of anhydrous active ingredient) |
| mannitol | 250 mg |
| water for the injection | 5 ml. |

Example B: An ointment comprising 0.05% by weight of active ingredient.

| Composition | Percent by weight |
|---|---|
| active ingredient | 0.05 |
| vaseline | 45.00 |
| paraffin oil | 19.60 |
| cetyl alcohol | 5.00 |
| beeswax | 5.00 |
| sorbitane sesquioleate | 5.00 |
| p-hydroxybenzoic acid ester | 0.20 |
| demineralised water | 20.15 |

The fatty substances and emulsifiers are melted together. The preservative is dissolved in water and the solution is emulsified into the melted fat at elevated temperature. After cooling, a suspension of the active ingredient is worked into part of the melted fat.

Example C: Tablets, comprising 50 mg of active ingredient each.

| Composition (10000 tablets) | |
| --- | --- |
| active ingredient | 500.0 g |
| lactose | 500.0 g |
| potato starch | 352.0 g |
| gelatin | 8.0 g |
| talcum | 60.0 g |
| magnesium stearate | 10.0 g |
| silicium dioxide (highly dispersed) | 20.0 g |
| ethanol | q.s. |

The active ingredient is mixed with the lactose and 292 g of the potato starch and the mixture is moistened with an ethanolic solution of the gelatin and granulated through a sieve. After drying, the remaining potato starch, the magnesium stearate, the talcum and the silicium dioxide are admixed and the mixture is compressed to tablets, each weighing 145 mg and having an active ingredient content of 50 mg, and these tablets may, if desired, be provided with breaking notches to allow the dosage to be more finely adjusted.

Example D: Film-coated tablets, comprising 100 mg of active ingredient each.
Composition (1000 film-coated tablets)

| active ingredient | 100.0 g |
| --- | --- |
| lactose | 100.0 g |
| corn starch | 70.0 g |
| talcum | 8.5 g |
| calcium stearate | 1.5 g |
| hydroxypropylmethylcellulose | 2.36 g |
| shellac | 0.64 g |
| water | q.s. |
| dichloromethane | q.s. |

The active ingredient, the lactose and and 40 g of the corn starch a mixed. The mixture is moistened with a paste, prepared from 15 g of corn starch and water (with heating) and granulated. The granulate is dried and the remaining corn starch, the talcum and the calcium stearate are mixed with the granulate. The mixture is compressed to tablets (weight: 280 mg each) which are then film-coated with a solution of the hydroxypropylmethylcellulose and the shellac in dichloromethane (final weight of the film-coated tablets: 283 mg each).

Example E: Gelatin dry-filled capsules, comprising 100 mg of active ingredient each.
Composition (1000 capsules)

| active ingredient | 100.0 g |
| --- | --- |
| lactose | 250.0 g |
| microcrystalline cellulose | 30.0 g |
| sodium lauryl sulfate | 2.0 g |
| magnesium stearate | 8.0 g |

Using a sieve having a mesh size of 0.2 mm, the sodium lauryl sulfate is sieved to the lyophilised active ingredient. Both components are intimately mixed. First the lactose is sieved to this mixture, using a sieve having a mesh size of 0.6 mm, and then the micro-cryistalline cellulose, using a sieve having a mesh size of 0.9 mm. All four components are then intimately mixed for 10 minutes. The magnesium stearate is sieved to this mixture last, using a sieve having a mesh size of 0.8 mm. After further mixing (3 minutes), 390 mg each of the formulation so obtained are filled into size 0 gelatin dry-filled capsules.

Example F: An injection or infusion solution, comprising 5 mg of active ingredient per 2.5 ml ampoule.
Composition (1000 ampoule)

| active ingredient | 5.0 g |
| --- | --- |
| sodium chloride | 22.5 g |
| phosphate buffer solution (pH: 7.4) | 300.0 g |
| demineralised water | ad 2500.0 ml |

The active ingredient and the sodium chloride are dissolved in 1000 ml of demineralised water. The solution is filtered through a microfilter. The filtrate is charged with the phosphate buffer solution and the mixture is bulked to 2500 ml with demineralised water. Dosage unit forms are prepared by filling 2.5 ml each of the mixture into glass ampoules which will then contain 5 mg of active ingredient each.

What is claimed is:

1. A method of treating navicular disease in horses, which comprises administering to a horse in need of such treatment an effective therapeutic amount of at least one compound of formula

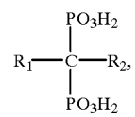

(I)

wherein $R_1$ is hydrogen, hydroxy, amino or halogen, and $R_2$ is hydrogen, halogen or a radical which is bound through C, N, S or O, or of a $C_1$–$C_4$tetraalkyl ester thereof, each in the free form, in the form of the salt and/or in the hydrate form.

2. A method according to claim 1, which comprises using a compound of formula I, wherein $R_1$ and $R_2$ are each independently of the other halogen, or $R_1$ is hydrogen, $R_2$ is a Ar—S—, Het—NH—, $C_3$–$C_7$cycloalkyl-NH—, Ar—S—A—N($R_3$)—, Het—S—A—N($R_3$)— or —C(=S)NHC$_6$H$_5$ group, A is linear or branched $C_1$–$C_{12}$alkyl, Ar is unsubstituted or substituted phenyl, Het is unsubstituted or substituted monocyclic 5- or 6-membered monoaza-, diaza- or thiazaaryl, which is bound through a ring-carbon atom or a ring-nitrogen atom, $R_3$ is hydrogen or $C_1$–$C_{12}$alkyl; or $R_1$ is hydrogen or hydroxy, $R_2$ is $R_4$—A—, $R_4$ is Ar, Het or —N($R_5$)($R_6$), A is linear or branched $C_1$–$C_{12}$alkyl, Ar is unsubstituted or substituted phenyl, and Het is unsubstituted or substituted monocyclic 5- or 6-membered monoaza-, diaza- or thiazaaryl, which is bound through a ring-carbon atom or a ring-nitrogen atom, $R_5$ and $R_6$ are each independently of the other hydrogen, $C_1$–$C_6$alkyl, $C_3$–$C_7$cycloalkyl, Ar—$C_1$–$C_6$alkyl, Ar—O—C$_1$–C$_6$alkyl, Ar—S—C$_1$–C$_6$alkyl or Het—C$_1$–C$_6$alkyl, or two alkyl R$_5$ and R$_6$ together form a 4- to 7-membered bridge which is unsubstituted or substituted by Ar and wherein two carbon atoms can by linked by a further C$_1$–C$_6$alkyl bridge, or 5-benzoyl-3,4-dihydro-2H-pyrazole-3,3-diphosphonic acid tetraethyl ester or (N-{4-phenylthio-n-butyl}) aminomethanediphosphonic acid tetraethyl ester.

3. A method according to claim 1, which comprises using a compound of formula I, wherein R$_1$ and R$_2$ are each independently of the other chloro, bromo or iodo.

4. The method according to claim 2 wherein R$_1$ is hydrogen, and R$_2$ is Ar—S—, Het—NH—, cyclo-C$_3$–C$_7$NH—, Ar—S—A—NH—, Het—S—A—NH— or C$_6$H$_5$—NHC(=S)—, A is linear or branched C$_1$–C$_6$alkyl, Ar is unsubstituted phenyl or phenyl which is independently of one another substituted by one or two C$_1$–C$_4$alkyl, C$_1$–C$_4$alkoxy, trifluoromethyl or halogen, Het is unsubstituted thiazolyl or pyridyl, or thiazolyl or pyridyl which is substituted by C$_1$–C$_4$alkyl.

5. A method according to claim 2, which comprises using a compound of formula I, wherein R$_1$ is hydrogen or hydroxy, R$_2$ is R$_4$—A—, R$_4$—N(R$_5$)(R$_6$), and R$_5$ and R$_6$ are each independently of the other hydrogen, C$_1$–C$_4$alkyl, cyclo-C$_3$–C$_7$alkyl, Ar—C$_1$–C$_4$alkyl, Ar—O—C$_1$–C$_4$alkyl, Ar—S—C$_1$–C$_4$alkyl or pyridyl-C$_1$–C$_4$alkyl, or wherein two alkyl R$_5$ and R$_6$ together form a 4- to 7-membered bridge which is unsubstituted or substituted by Ar and wherein two carbon atoms can be linked to each other by a further C$_1$–C$_6$alkyl bridge.

6. The method according to claim 2, wherein the compound of formula I comprises at least one of the compounds (1) 3-amino-1-hydroxypropane-1,1-diphosphonic acid; or
(2) 3-(N,N-dimethylamino)-1-hydroxypropane-1,1-diphosphonic acid; or
(3) 4-amino-1-hydroxybutane-1,1-diphosphonic acid; or
(4) 6-amino-i-hydroxyhexane-1,1-diphosphonic acid; or
(5) 3-(N-methyl-N-n-pentylamino)-1-hydroxypropane-1,1-diphosphonic acid; or
(6) 1-hydroxy-2-(imidazol-1-yl)ethane-1,1-diphosphonic acid; or
(7) 1-hydroxy-2-(pyrid-3-yl)ethane-1,1-diphosphonic acid; or
(8) 4-chlorophenylthiomethanediphosphonic acid; or
(9) 3-(N-2-phenylthioethyl-N-methylamino)-1-hydroxypropane-1,1-diphosphonic acid; or
(10) 1-hydroxy-3-pyrrolidin-1-yl)propane-1,1-diphosphonic acid; or
(11) 3-(3-[4-chlorophenyl]pyrrolidin-1-yl)1-hydroxypropane-1,1-diphosphonic acid; or
(12) (N-cycloheptylamino)methanediphosphonic acid; or
(13) (N-phenylaminothiocarbonyl)methanediphosphonic acid; or
(14) 5-benzoyl-3,4-dihydro-2H-pyrazole-3,3-diphosphonic acid tetraethyl ester; or
(15) 1-hydroxy-2-(imidazo[1,2-a]pyridin-3-yl)ethane-1,1-diphosphonic acid; or
(16) dichloromethanediphosphonic acid; or
(17) 3-(N-methyl-N-3-phenyl-n-propylamino)-1-hydroxypropane-1,1-diphosphonic acid; or
(18) 3-(N-methyl-N-5-phenyl-n-pentylamino)-1-hydroxypropane-1,1-diphosphonic acid; or
(19) 3-(N-methyl-N-[5-pyrid-2-yl]-n-pentylamino)-1-hydroxypropane-1,1-diphosphonic acid; or
(20) 3-(N-methyl-N-[3-phenoxy]-n-propyl-amino)-1-hydroxypropane-1,1-diphosphonic acid; or
(21) 3-(N-methyl-N-[2-phenoxy]ethylamino)-1-hydroxypropane-1,1-diphosphonic acid; or
(22) 4-(4-phenyl)piperidin-1-yl-1-hydroxybutane-1,1-diphosphonic acid; or
(23) 1-hydroxy-3-piperidin-1-yl-propane-1,1-diphosphonic acid; or
(24) 3-(4-[4-chlorophenyl]piperidin-1-yl)-1-hydroxypropane-1,1-diphosphonic acid; or
(25) (5-n-butyl)thiazol-2-yl-methanediphosphonic acid; or
(26) (5-methyl)thiazol-2-yl-methanediphosphonic acid; or
(27) thiazol-2-yl-methanediphosphonic acid; or
(28) (5-ethyl)thiazol-2-yl-methanediphosphonic acid; or
(29) 1-hydroxy-(N-[2-phenyl]ethyl-N-methylamino)propane-1,1-diphosphonic acid; or
(30) 3-(N-methyl-N-[3-phenylthio]-n-propylamino)-1-hydroxypropane-1,1-diphosphonic acid; or
(31) 2-(N,N-dimethylamino)-1-hydroxyethane-1,1-diphosphonic acid; or
(32) 3-(N-methyl-N-n-propylamino)-1-hydroxypropane-1,1-diphosphonic acid; or
(33) 1-hydroxy-3-(N-[3-phenylthio]n-propyl-N-methylamino)propane-1,1-diphosphonic acid; or
(34) 1-hydroxy-3-(N-[4-phenylthio]n-butyl-N-methylamino)propane-1,1-diphosphonic acid; or
(35) 2-(1-methyl)imidazol-2-yl-ethane-1,1-diphosphonic acid; or
(36) 1-hydroxy-2-(4-methyl)imidazol-5-yl-ethane-1,1-diphosphonic acid; or
(37) 1-hydroxy-2-(imidazol-5-yl)ethane-1,1-diphosphonic acid; or
(38) 2-(pyrid-2-yl)ethane-1,1-diphosphonic acid; or
(39) 3-(1,5-dimethyl-3-azabicyclo[3.1.1]hept-3-yl)-1-hydroxypropane-1,1-diphosphonic acid; or
(40) (4-phenylthio-n-butylamino)methanediphosphonic acid tetraethyl ester.

7. The method according to claim 1 which comprises administering to the horse from 0.1 mg to 200 mg of at least one compound of formula I per kg of body weight.

8. The method according to claim 4 wherein

R$_1$ is hydrogen, and

R$_2$ is C$_6$H$_5$—NHC(=S)—, unsubstituted or chloro-substituted phenylthio, unsubstituted or C$_1$–C$_4$alkyl-substituted thiazolylamino or cycloheptylamino.

* * * * *

UNITED STATES PATENT AND TRADEMARK OFFICE
CERTIFICATE OF CORRECTION

PATENT NO    : 6,057,306
DATED:       : May 2, 2000
INVENTOR(S)  : Alan Martin Wilson, et al.

It is certified that there is an error in the above-identified patent and that said Letters Patent is hereby corrected as shown below:

Claim 6, line 7, number (4), should be:

6-amino-1-hydroxyhexane-1,1-diphosphonic acid; or

Signed and Sealed this

Tenth Day of April, 2001

Attest:

NICHOLAS P. GODICI

Attesting Officer          Acting Director of the United States Patent and Trademark Office